United States Patent [19]
Feldman et al.

[11] Patent Number: 5,591,831
[45] Date of Patent: Jan. 7, 1997

[54] SOLUBILIZATION AND PURIFICATION OF THE ACTIVE GASTRIN RELEASING PEPTIDE RECEPTOR

[75] Inventors: Richard I. Feldman; James M. Wu, both of El Cerrito; Elaina Mann; Anne Larocca, both of San Leandro; James C. Jenson, Moraga, all of Calif.

[73] Assignee: Berlex Laboratories, Inc.

[21] Appl. No.: 186,351

[22] Filed: Jan. 25, 1994

Related U.S. Application Data

[62] Division of Ser. No. 879,825, May 7, 1992, abandoned, which is a division of Ser. No. 426,150, Oct. 24, 1989, Pat. No. 5,215,963.

[51] Int. Cl.$^6$ ................................................. C07K 14/705
[52] U.S. Cl. .......................... 530/395; 530/350; 530/412; 435/69.1
[58] Field of Search ..................................... 530/350, 395, 530/412; 435/69.1

[56] References Cited

U.S. PATENT DOCUMENTS 4,761,371  8/1988  Bell .......................................... 435/68

FOREIGN PATENT DOCUMENTS 0339193    2/1989   European Pat. Off. .
WO88/07551 10/1988  WIPO .
89/09232    5/1989   WIPO .

OTHER PUBLICATIONS

Penella J. Woll, et al. (1988) "[D-Arg$^1$, D-Phe$^5$, D-Trp$^{7,9}$, Leu$^{11}$] substance P, a potent bombesin antagonist in murine Swiss 3T3 cells, inhibits the growth of human small cell lung cancer cells in vitro", *Proc. Natl. Acad. Sci. USA*, 85:1859–1863.
Steen E. Pedersen, et al. (1985) "Functional Activation of β–Adrenergic Receptors by Thiols in the Presence or Absence of Agonists", *The Journal of Biological Chemistry*, 260:14150–14157.
Ian Zachary, et al. (1985) "High–affinity receptors for peptides of the bombesin family in Swiss 3T3 cells", *Proc. Natl. Acad. Sci. USA*, 82:7616–7620.
Terry W. Moody, et al. (1985) "High Affinity Receptors for Bombesin/GRP–Like Peptides on Human Small Cell Lung Cancer", *Life Sciences*, 37:105–113.
Frank Cuttitta, et al. (1985) "Bombesin–like peptides can function as autocrine growth factors in human small–cell lung cancer", *Nature*, 316:823–826.
Yutaka Yanagita, et al. (1986) "Solubilization and purification of membrane proteins," *Techniques for the Analysis of Membrane Proteins*, Chapter 3, eds. C. I. Ragan & R. J. Cherry (London: Chapman and Hall), 61–77.
Sheridan L. Swope, et al. (1987) "Characterization of ligand binding and processing by bombesin receptors in an insulin–secreting cell line", *Biochem. J.*, 247:731–738.
Ian Zachary, et al. (1987) "A Role for Neuropeptides in the Control of Cell Proliferation", *Developmental Biology*, 124:295–308.

Richard M. Kris, et al. (1987) "Identification of the Bombesin Receptor on Murine and Human Cells by Cross–linking Experiments", *The Journal of Biological Chemistry*, 262:11215–11220.
Yasuo Masu, et al. (1987) "cDNA cloning of bovine substance–K receptor through oocyte expression system", *Nature*, 329:836–838.
James B. Fischer, et al. (1988) "The Bombesin Receptor Is Coupled to a Guanine Nucleotide–binding Protein Which Is Insensitive to Pertussis and Cholera Toxins", *The Journal of Biological Chemistry*, 263:2808–2816.
John D. Minna, et al. (1988) "Gastrin–Releasing Peptide and Other Autocrine Growth Factors in Lung Cancer: Pathogenetic and Treatment Implications," *Important Advances in Oncology*, Chapter 4, (Philadelphia: J. B. Lippincott Co.), 55–64.
Anders Sundan (1988) "Identification of the Bombesin Receptor by Monoclonal Anti–Idiotypic Antibodies", Symposium on Growth Factors and the Receptors: Genetic Control and Rational Application, held at the 17th Annual Meeting of the UCLA Symposia on Molecular and Cellular Biology, Keystone, Colorado, USA, Jan. 24–30, 1988, *J. Cell Bio–chem. Suppl.*, vol. 0, No. 12, Part A, p. 116.
H. G. Khorana (1988) "Bacteriorhodopsin, a Membrane Protein That Uses Light to Translocate Protons", *The Journal of Biological Chemistry*, 263:7439–7442.
James Sinnett–Smith, et al. (1988) "Characterization of a Bombesin Receptor on Swiss Mouse 3T3 Cells by Affinity Cross–Linking", *Journal of Cellular Biochemistry*, 38:237–249.
Jean Mazella, et al. (1988) "Solubilization and Characterization of Active Neuortensin Receptors from Mouse Brain", *The Journal of Biological Chemistry*, 263:144–149.
Kenneth D. Brown, et al. (1988) "Characterization of the high–affinity receptors on Swiss 3T3 cells which mediate the binding, internalization and degradation of the mitogenic peptide bombesin", *Biochem. J.*, 252:227–235.
Wolfgang Meyerhof, et al. (1988) "Expression and electrophysiological identification of the receptor for bombesin and gastrin–releasing peptide in *Xenopus laevis* oocytes injected with polyA$^+$RNA from rat brain", *FEB Letters*, 239:109–112.
Wolf, Steven S. et al. (1985) "Receptors for GRP/Bombesin–Like Peptides in the Rat Forebrain", *Peptides* 6:111–114.
Zachary, Ian, et al. (1987) "Identification of a Receptor for Peptides of the Bombesin Family in Swiss 3T3 Cells by Affinity Cross–linking", *The Journal of Biological Chemistry*, 262:3947–3950.

(List continued on next page.)

*Primary Examiner*—Stephen G. Walsh
*Assistant Examiner*—Sally P. Teng
*Attorney, Agent, or Firm*—Townsend and Townsend and Crew LLP

[57] ABSTRACT

A procedure for the preparation of the solubilized and purified gastrin releasing peptide receptor, in an active form, from a gastrin releasing peptide receptor source such as Swiss 3T3 fibroblasts.

14 Claims, 3 Drawing Sheets

OTHER PUBLICATIONS

Spindel, E. R., et al. (1989) "Expression in Xenopus Oocytes of Functional Bombesin/GRP Receptors Transcribed From A Bacteriophage cDNA Library", *19th Annual Meeting Of The Society For Neuroscience*, Oct. 29, Nov. 3, 1989, Society Neuroscience Abstract 15:345.

Gaudino, Giovanni, et al. (date: illegible) "A Tyrosine Protein Kinase Activated by Bombesin in Normal Fibroblasts and Small Cell Carcinomas", *Annals New York Academy of Sciences*, 293–302.

Gaudino, G., et al. (1988) "Activation of the protein-tyrosine kinase associated with the bombesin receptor complex in small cell lung carcinomas", *Proc. Natl. Acad. Sci.*, 85:2166–2170.

Zachary, Ian, et al. (1987) "Inhibition of Bombesin–Induced Mitogenesis by Pertussis Toxin: Dissociation From Phospholipase C Pathway", *Biochemical and Biophysical Research Communications*, 146:456–463.

Letterio, John J., et al. (1986) "Pertussis Toxin–Sensitive Pathway in the Stimulation of c–myc Expression and DNA Synthesis by Bombesin" *Science*, 117–119.

Cirillo, Daniela M., et al. (1986) "Receptor for Bombesin with Associated Tyrosine Kinase Activity", *Molecular and Cellular Biology*, 6:4641–4649.

SOLUBILIZATION AND PURIFICATION OF THE ACTIVE GASTRIN RELEASING PEPTIDE RECEPTOR

This is a Division of application Ser. No. 07/879,825 filed May 7, 1992, now abandoned, which is a divisional of application Ser. No. 07/426,150 filed Oct. 24, 1989, now issued on Jun. 1, 1993 as U.S. Pat. No. 5,215,963.

BACKGROUND OF THE INVENTION

Growth factors are involved in numerous physiological and pathological processes. An increasing number of small regulatory peptides have been discovered in the neural and neuroendocrine cells of mammalian tissues. More recent evidence has pointed to the role of neuropeptides in the regulation of animal cell growth, and in particular to the action of mitogenic peptides in the Swiss 3T3 cell system. One of the first neuropeptides studied was the tetradecapeptide bombesin which was originally isolated from amphibian skin, Anastasi et al., Experientia 27:166–167 (1971). Bombesin is structurally related to several endogenous mammalian peptides, the first to be characterized being gastrin releasing peptide.

Gastrin releasing peptide (GRP) is a 27 amino acid peptide having the following sequence in humans: Val-Pro-Leu-Pro-Ala-Gly-Gly-Gly-Thr-Val-Leu-Thr-Lys-Met-Tyr-Pro-Arg-Gly-Asn-His-Trp-Ala-Val-Gly-His-Leu-Met-$NH_2$. GRP is of significant interest because of its presumed ability to function as an autocrine growth factor in the pathogenesis of cancer. In particular, GRP has been found to promote growth of human small cell lung carcinoma (SCLC). GRP binding to cell surface receptors is thought to stimulate cellular growth by promoting the hydrolysis of phosphatidyl inositides and by activation of protein kinase C. A large number of biological responses to GRP have been observed including stimulation of $Na^+/H^+$ antiport, mobilization of intracellular $Ca^{2+}$, amplification of c-fos and c-myc oncogenes, induction of tyrosine kinase activity, elevation of DNA synthesis and promotion of cell division.

The role of GRP in maintaining the growth of SCLC suggests that effective therapeutic agents could be developed that interrupt the autocrine growth cycle by inactivating GRP or inhibiting its receptor. The active site of GRP is the C-terminal region which binds high affinity receptors on SCLC membranes. Blocking this binding can inhibit SCLC growth. This has already been accomplished with monoclonal antibodies to bombesin which bind to the active site on GRP, thus inactivating the peptide, Cuttitta et al., Nature 316:823–826 (1985).

Another means to block GRP binding to its receptor, and therefore to treat SCLC, is to inhibit the receptor itself. This can be accomplished by use of agents which bind to the GRP receptor and act as antagonists. Antagonists can normally be found once the receptor has been pharmacologically defined, as is the case with the GRP receptor. Testing of potential receptor antagonists has been made much easier with the development of highly automated assay methods. Unfortunately, these systems require purified GRP receptor in an active form, which has not been readily attainable. This problem can be overcome by use of the recombinant receptor. Along with providing an improved renewable source of the receptor from a specific source, using the recombinant GRP receptor in screening for GRP receptor reactive drugs also has the following advantages: potentially greater number of receptors per cell giving greater yield of reagent and higher signal to noise ratio in assays; and receptor subtype specificity (theoretically giving greater biological and disease specificity).

Cross-linking of the GRP receptor to bound radiolabeled GRP has been used to visualize the GRP receptor-ligand conjugate on SDS-PAGE and to deduce certain other characteristics of the receptor Rosengurt et al., PCT/GB88/00255. However, the technique used did not involve isolation of the receptor but rather involved characterization of a modified form of the receptor protein. Unfortunately, in order to characterize the structural properties of the GRP receptor in greater detail and to understand the mechanism of action at the molecular level, the receptor needs to be purified. For some applications, it is essential to purify the receptor in an active state which maintains the binding activity of the receptor. These include the generation of antibodies against active receptor epitopes, structural studies of the ligand binding site, and the use of the purified receptor for screens for agonists and antagonists of GRP binding.

To date, few receptors have been isolated and characterized in their active form. There are two main reasons for this. First, the amount of receptor present in most tissues is minute and second, the receptor must often be solubilized from membranes with detergents that can perturb the structure of the protein. Further compounding these difficulties is the unpredictable nature of receptors in that the method for successfully solubilizing one protein receptor may not be successful for a different protein receptor.

SUMMARY OF THE INVENTION

This invention pertains to the solubilization of the active GRP receptor from cellular membranes, the characterization of receptor behavior in solution and the purification of the solubilized receptor in an active form, with the extracted receptor retaining full GRP binding activity.

More specifically, this invention pertains to the use of the active solubilized GRP receptor, the active solubilized and purified GRP receptor, and transfected cell lines and membranes from such cell lines, in drug screening assays for compounds having suitable binding affinity for the GRP receptor.

Even more specifically, this invention pertains to the active GRP receptor both in the solubilized, unpurified and in the solubilized, purified form, along with protein fragments of the receptor and antibodies directed thereto that may be useful in diagnostic assays to determine if a patient has elevated levels of the gastrin releasing peptide receptor. Assays based on detection of antibodies to the GRP receptor and/or detection of the GRP receptor itself may also have prognostic value.

Additionally, this invention pertains to using the solubilized and purified GRP receptor or fragments or derivatives thereof such as antibodies to the receptor or fragments, as therapeutic agents.

DETAILED DESCRIPTION OF THE INVENTION

This invention provides a means for solubilizing the active gastrin releasing peptide (GRP) receptor from a source of GRP receptor using a stabilizing agent and a detergent. As used herein, the term "active" is used to mean activity with respect to gastrin releasing peptide binding.

The stabilizing agent is preferably a soluble cholesteryl ester. Particularly good results have been obtained using cholesteryl hemisuccinate (CHS). The detergent can be non-ionic, zwitter-ionic or the like. Particularly good results have been obtained using the zwitter-ionic detergent 3-[(3-cholamidopropyl)dimethylammonio]-1-propane sulfonate (CHAPS).

The source of GRP receptor can be a eukaryotic or prokaryotic host expressing recombinant GRP receptor, such as is described in Stefano Marullo et al., Bio/Technology 7:923–927 (September, 1989). The source can also be a cell line such as mouse Swiss 3T3 fibroblasts, but other mammalian cell lines are also contemplated by this invention, with the preferred cell line being human.

Cellular membranes containing the GRP receptor are prepared by lysis of a cultured GRP receptor containing cell line such as Swiss 3T3 fibroblasts, followed by centrifugation. The resulting pellets are washed by resuspension and centrifuged again.

Once the membranes are obtained from a suitable cell line as described above and in Example 1, the final concentration of protein is adjusted. A suitable final protein concentration is about 15 mg/ml.

The membranes are then salt washed prior to solubilization of the GRP receptor. The membranes are washed twice with buffer and NaCl, then washed with a solubilization buffer and finally suspended in the solubilization buffer at an adjusted protein concentration. A suitable buffer composition for the first two washings comprises a medium such as 50 mM 4-(2-hydroxyethyl)-1-piperazine ethane sulfonic acid (HEPES), pH 7.5, a chelator such as 2 mM ethylenediamine-tetraacetic acid (EDTA), and protease inhibitors. A suitable NaCl concentration is 1.0M. The solubilization buffer, both for the washing and suspension, can be typically comprised of 50 mM HEPES, pH 7.5, 2 mM EDTA, another chelator such as 1 mM [ethylenebis-(oxyethylenenitrilo)] tetraacetic acid (EGTA), 100 mM NaCl and protease inhibitors. The protein concentration is adjusted to about 7 mg/ml, for example. This salt washing step provides a 2 fold purification. Similar results can be achieved by washing the membranes with 2M urea, high pH buffers (pH 10) or chaotropic salts such as KI. This procedure also increases the stability of the GRP receptor in the extract. Other constituents of the buffers may include, for example, sucrose, and suitable protease inhibitors include, without limitation, aprotinin, leupeptin, pepstatin, bacitrin and phenylmethylsulfonyl fluoride (PMSF).

A mixture of detergent (CHAPS) and soluble cholesteryl ester stabilizing agent (CHS) is then slowly added to the membrane suspension to give a set final detergent concentration. The weight ratio of detergent to soluble cholesteryl ester can be within the range of about 200:1 to 5:2, preferably about 10:1. Alternatively, the detergent can be added to the membrane suspension, followed by the addition of the soluble cholesteryl ester. In that instance, initially there will be 100% detergent and the soluble cholesteryl ester is added until the weight ratio of detergent to ester is within the range of about 200:1 to 5:2, preferably about 10:1. For solubilization of the GRP receptor, the concentration of detergent should be 0.4 to 3.0% (w/v), and is optimally set at about 0.75% (w/v) for a membrane concentration (prior to the membrane washing steps) of around 15 mg/ml. Similarly, the concentration of soluble cholesteryl ester is within the range of about 0.0015% to 1.2% (w/v). Likewise, for a membrane concentration of around 15 mg/ml, the concentration of soluble cholesteryl ester is preferably about 0.0754% (w/v).

The extract is then incubated at a temperature within the range of about 0° to 37° C., typically room temperature such as 21° C., and then cooled to 0° to 21° C., typically 4° C., and the insoluble material centrifuged at high speeds, preferably about 100,000 times gravity, in a standard centrifuge for a suitable period of time depending upon the volume involved to obtain an extract containing the solubilized receptor (i.e., soluble extract).

At the high detergent concentration (0.4 to 3.0%), the receptor is not active. However, upon dilution with a buffer solution, the receptor is reactivated. The presence of the soluble cholesteryl ester, which acts as a stabilizing agent, is necessary for the receptor to be reactivated at the low detergent concentration. For assays using the active solubilized GRP receptor, to exhibit binding activity the final concentration of detergent in the suspension should be diluted to within the range of about 0.025 to 0.2% (w/v). The weight ratio of detergent to soluble cholesteryl ester is still maintained within the range of about 200:1 to 5:2, preferably about 10:1. Therefore, a suitable range for the soluble cholesteryl ester is about 0.000125% to 0.08% (w/v). The preferable assay concentrations are 0.075% (w/v) detergent and about 0.0075% (w/v) soluble cholesteryl ester.

This invention further provides for purifying the solubilized receptor in its active form and free of contaminating proteins. Purification of the GRP receptor involves a multistep procedure which includes the following steps, which follow the solubilization procedure set forth above.

(1) Polyethylene glycol precipitation. The GRP receptor is precipitated from the soluble extract by addition of polyethylene glycol (PEG). Addition of PEG is preferably done to obtain a final concentration of 20% (w/v). The precipitate is then collected by centrifugation and resuspended in a buffer solution. The buffer solution can typically be comprised of 25 mM HEPES, pH 7.5, 25 mM Tris/Cl, 2 mM EDTA, 0.075% (w/v) detergent, 0.0075% (w/v) soluble cholesteryl ester, and protease inhibitors. The final volume of the suspension is preferably 25% that of the original soluble extract. Proteins remaining insoluble in the suspension are removed by centrifugation. This step provides a 2 fold purification, and enhances the stability of the receptor.

(2) Wheat germ agglutinin chromatography. The soluble extract is applied to a wheat germ agglutinin affinity column equilibrated with a buffer solution typically comprised of 50 mM HEPES, pH 7.5, 2 mM EDTA, 0.25% (w/v) detergent, 0.025% (w/v) cholesteryl ester and protease inhibitors. The column is eluted with column buffer solution and 5 mM N-N'-N"-triacetyl-chitotriose. Fractions containing the GRP receptor are then identified by $^{125}$I-GRP binding assays. This step provides a 5 fold purification by removing proteins that do not contain carbohydrate. To obtain a good yield, it is necessary to elute the column with chitotriose or chitobiose. The yield may also be enhanced by maintaining the detergent concentration above about 0.2% detergent and 0.02% soluble cholesteryl ester.

(3) GRP-affinity chromatography. The Seat gem agglutinin column eluate is further fractionated on a GRP affinity column. In the preferred embodiment, the column contains a beaded matrix with the peptide human [Nle$^{14,27}$]GRP13-27 (the C-terminal portion of GRP) coupled to it at 2 mg peptide/ml packed gel. The column is equilibrated with a solution typically comprised of 25 mM Tris, 25 mM HEPES, pH 7.5, 2 mM EDTA, 0.075% (w/v) CHAPS, 0.0075% (w/v) CHS and protease inhibitors. The concentration of detergent in the wheat germ agglutinin column eluate is preferably adjusted to 0.075% (w/v) by dilution with a solution typically comprised of 25 mM HEPES, 25 mM Tris, pH 7.5, 2 mM EDTA and protease inhibitors. After application of the sample and extensive washing of the column, bound protein is eluted with a salt at a concentration above 0.2M. Particularly suitable is 0.5M NaCl. Fractions containing the GRP receptor are then identified by $^{125}$I-GRP binding assays. The GRP peptide used ([Nle$^{14,27}$]GRP13-27) is an analog made by Triton Biosciences Inc. (Alameda, Calif.) which is resistant to oxidation. Other GRP peptides and matrixes that will also work include, without limitation, GRP1-27, GRP14-27 and [Lys$^3$]Bombesin. However the yield and elution conditions may be altered. Elution of the bound protein with salt is important because receptor binding activity is preserved and a good yield is achieved. The concentration of detergent in the sample loaded onto the column is critical for optimal results. The suitable range of detergent is about 0.025% to 0.24% (w/v). The ratio of detergent to stabilizing agent is also the same, being 200:1 to 5:2, preferably 10:1.

(4) Second affinity column. Fractions containing the GRP receptor eluted from the affinity column are desalted and the sample is applied to a second GRP affinity column, and eluted as described in step (3). Fractions containing the receptor are then identified by binding assays. Use of two consecutive affinity columns in this step is required to give a high degree of purity.

(5) Gel filtration. This is an optional step that yields a marginally purer product. The gel filtration step is also useful to remove protease inhibitors, salt and residual detergent from the receptor.

In general, the solubilized, unpurified and solubilized, purified GRP receptor of this invention binds gastrin releasing peptide with an affinity of at least $K_D$=10 nM. The GRP receptor from a mouse Swiss 3T3 fibroblast cell line, according to this invention was found to have the following characteristics:

runs as a broad band on SDS-PAGE with an apparent molecular weight of about 70 to 100 kilodaltons;

binds selectively with polypeptides of the bombesin type;

has a $K_D$ value of about 10–100 pM;

is free of coupled G proteins;

contains N-linked carbohydrates;

when deglycosylated, has an apparent molecular weight of 36±5 kilodaltons on SDS-PAGE; and has a partial amino acid sequence near the N-terminus of:

-Leu-Asn-Leu-Asp-Val-Asp-Pro-Phe-Leu-Ser-

This invention also contemplates the determination of both the protein (amino acid) sequence and the DNA (nucleotide) sequence of the GRP receptor. As noted above, a partial amino acid sequence near the N-terminus has been identified:

-Leu-Asn-Leu-Asp-Val-Asp-Pro-Phe-Leu-Ser-

Since this invention teaches how to isolate the GRP receptor in its pure form, other amino acid sequences and nucleotide sequences are readily ascertainable by methods well known to those skilled in the art.

Partial amino acid sequences can also be used to deduce DNA probes which can be used to isolate the GRP receptor cDNA or genomic form of the gene. Some of the standard methods that can be used are described, or referenced in T. Maniatis et al., *Molecular Cloning, A Laboratory Manual* (Cold Spring Harbor Laboratory, Cold Spring Harbor, N.Y.), or F. M. Ausubel et al., *Biology* (Greene Publishing Associates, Brooklyn, N.Y.), all of which are incorporated herein by reference. cDNA libraries, usually maintained in *E. Coli*, are first constructed from RNA isolated from a suitable source that expresses the GRP receptor. A variety of approaches can be used to deduce DNA probes from the partial amino acid sequence of the GRP receptor, such as picking a nucleotide sequence based upon the most likely codon usage, synthesis of fully degenerate probes and the synthesis of probes containing the nucleotide Inosine at degenerate positions. The cDNA library is plated out to yield colonies of *E. Coli*, each containing individual cDNA clones, which are probed for GRP receptor cDNA sequences with labeled oligonucleotide probes. GRP receptor cDNAs isolated by this procedure, if not complete, can be used to isolate the full length cDNA. If desired, the GRP receptor gone can then be isolated from genomic DNA libraries. In addition, the GRP receptor cDNA, or portions of it, can be used to isolate GRP receptor cDNAs from other species, such as humans. In a similar fashion, other cDNAs for proteins which are highly homologous to the GRP receptor at the DNA level can be isolated.

An alternative method to isolate the GRP receptor cDNA is to use polymerase chain reaction technology to amplify a sequence of the GRP receptor cDNA from a complex mixture of cDNAs. Two DNA probes which are homologous to two different regions of the GRP receptor cDNA are used in the procedure. Only the region of DNA between the two probes is highly amplified, and can be readily isolated and characterized. One probe may be derived from the partial amino acid sequence that has been determined from the purified receptor, and the other probe could be deduced by picking a sequence that has been found to be conserved among the various members of the class of G-protein coupled receptors, to which the GRP receptor belongs.

Still another method of isolating the GRP receptor is to use the purified receptor, fragments thereof, or peptides constructed from the partial amino acid sequence of the receptor to generate antibodies that react with the GRP receptor. The antibodies can be used to probe expression libraries (for example λGT-11 libraries) that allow the translation of cDNAs into protein epitopes that can be recognized by the antibodies. In addition, antibodies recognizing the GRP receptor can be used to sort cells containing the GRP receptor, from those lacking it, for example by use of a Fluorescent Activated Cell Sorter. This method can be used to isolate the GRP receptor cDNA from a suitable host cell that has been transfected with a cDNA expression library.

Once the cDNA for the GRP receptor is isolated, from mouse for example, it can be sequenced using standard techniques. The nucleotide sequence would reveal the sequence of the primary translation product of the GRP receptor, i.e., the sequence before any post-translation modification.

The GRP receptor and any fragments thereof can be prepared by recombinant DNA techniques. Specific portions of the GRP receptor cDNA, deduced from protein sequence information, or the sequence of the GRP receptor cDNA, can be made by solid phase synthetic methods. Alternatively, the natural gene can be isolated by cDNA. The receptor cDNA is inserted at a suitable site in a cloning vehicle, vector, or plasmid. An appropriate organism, such as bacteria cells, yeast cells, or mammalian cells, is transfected with the expression vector to obtain expression of the GRP receptor or its fragments. Portions of the receptor may be expressed as fusions with other proteins. It is expected that the gene which codes for the gastrin releasing peptide receptor will be particularly useful to identify genes which code for related or homologous receptors, along with the genes which code for GRP receptor sub-types and for the GRP receptor in tissue of different species.

Once the sequence, or any portion thereof, is known, the GRP receptor or any fragments thereof can be prepared by conventional processes for synthesizing peptides. These include processes such as are described in John M. Stewart and Janis D. Young, *Solid Phase Peptide Synthesis* (Pierce Chemical Co., Rockford, Ill. 1984), M. Bodanszky and A. Bodanszky, *The Practice of Peptide Synthesis* (Springer-Verlag, New York, 1984) and M. Bodanszky, *The Principles of Peptide Synthesis* (Springer-Verlag, New York, 1984), all of which are incorporated herein by reference. For example, an azide process, an acid chloride process, an acid anhydride process, a mixed anhydride process, an active ester process (for example, p-nitrophenyl ester, N-hydroxysuccinimide ester, or cyanomethyl ester), a carbodiimidazole process, an oxidative-reductive process, or a DCC/additive process can be used. Solid phase and solution phase syntheses are both applicable to the foregoing processes.

The GRP receptor is suitably prepared in accordance with the above processes as typically employed in peptide synthesis, generally either by a so-called stepwise process which comprises condensing an amino acid to the terminal amino acid, one by one in sequence, or by coupling peptide fragments to the terminal amino acid. Amino groups that are not being used in the coupling reaction must be protected to prevent coupling at an incorrect location.

If a solid phase synthesis is adopted, the C-terminal amino acid is bound to an insoluble carrier or support through its carboxyl group. The insoluble carrier is not particularly limited as long as it has a binding capability to a reactive carboxyl group. Examples of such insoluble carriers include halomethyl resins, such as chloromethyl resin or bromomethyl resin, hydroxymethyl resins, phenol resins, tert-alkyloxycarbonylhydrazidated resins, and the like.

An amino group-protected amino acid is bound in sequence through condensation of its activated carboxyl group and the reactive amino group of the previously formed peptide or chain, to synthesize the peptide step by step. After synthesizing the complete sequence, the peptide is split off from the insoluble carrier to produce the peptide. This solid-phase approach is generally described by Merrifield, et al. in J. Am. Chem. Soc. 85:2149–2156 (1963), which is incorporated herein by reference.

The prepared receptor and fragments thereof can be isolated and purified from the reaction mixture by means of peptide separation, for example, by extraction, precipitation, electrophoresis and various forms of chromatography, and the like. The receptor of this invention can be obtained in varying degrees of purity depending upon its desired use. Purification can be accomplished by use of the protein purification techniques of this invention or by the use of the antibodies herein described in immunoabsorbant affinity chromatography. This immunoabsorbant affinity chromatography is carried out by first linking the antibodies to a solid support and then contacting the linked antibodies with solubilized lysates of small cell lung cancer cells, lysates of other cells expressing the GRP receptor, or lysates or supernatants of cells producing the GRP receptor as a result of DNA techniques described below.

The solubilized GRP receptor of this invention can be used as an immunogen for the production of antisera or antibodies specific for the receptor or any fragments thereof. The purified receptor can be used to screen monoclonal antibodies prepared by immunization with various forms of impure preparations containing the GRP receptor. The purified receptor can also be used as a reagent to detect any antibodies generated in response to the presence of elevated levels of gastrin releasing peptide receptor or cell fragments containing the GRP receptor. Additionally, GRP receptor fragments may also serve as immunogens to produce the antibodies of the present invention. For example, this invention contemplates raising antibodies to the GRP receptor partial amino acid sequence:

-Leu-Asn-Leu-Asp-Val-Asp-Pro-Phe-Leu-Ser-

Antibodies can be raised to the GRP receptor, and fragments thereof, both in its naturally occurring form and in its recombinant form. Additionally, antibodies can be raised to both the GRP receptor in its active form and in its inactive form, the difference being that antibodies to the active receptor recognize epitopes which are only present in the active receptor.

The antibodies of this invention can have significant therapeutic value. They can be used as neutralizing antibodies in that they can bind to the GRP receptor and either inhibit ligand binding to the receptor or inhibit biological responses. They also can be useful as non-neutralizing antibodies and can be coupled to toxins or radionuclides so that when the antibody binds to the receptor, the cell itself is killed.

The antibodies of this invention can also be useful in diagnostics. As capture or non-neutralizing antibodies, they can bind to the GRP receptor without inhibiting ligand binding. As neutralizing antibodies, they can be useful in competitive binding assays.

Receptor fragments may be joined to other materials, particularly polypeptides, as fused or covalently joined polypeptides to be used as immunogens. The GRP receptor and its fragments may be fused or covalently linked to a variety of immunogens, such as keyhole limpet hemocyanin, bovine serum albumin, tetanus toxoid, etc. See for example, *Microbiology*, Hoeber Medical Division (Harper and Row, 1969), Landsteiner, *Specificity of Serological Reactions* (Dover Publications, New York, 1962) and Williams et al., *Methods in Immunology and Immunochemistry, Vol.* 1 (Academic Press, New York, 1967), all of which are incorporated herein by reference, for descriptions of methods of preparing polyclonal antisera. A typical method involves hyperimmunization of an animal with an antigen. The blood of the animal is then collected shortly after the repeated immunizations and the gamma globulin is isolated.

In some instances, it is desirable to prepare monoclonal antibodies from various mammalian hosts, such as mice, rodents, primates, humans, etc. Description of techniques for preparing such monoclonal antibodies may be found in, Stites et al., editors, *Basic and Clinical Immunology*, (Lange Medical Publications, Los Altos, Calif., Fourth edition) and references cited therein, and in particular in Kohler and Milstein in Nature 256: 495–497 (1975), which discusses one method of generating monoclonal antibodies. Summarized briefly, this method involves injecting an animal with an immunogen. The animal is then sacrificed and cells taken from its spleen, which are then fused with myeloma cells. The result is a hybrid cell or "hybridoma" that is capable of reproducing in vitro. The population of hybridomas is then screened to isolate individual clones, each of which secrete a single antibody species to the immunogen. In this manner, the individual antibody species obtained are the products of single B cells from the immune animal generated in response to a specific site recognized on the immunogenic substance.

The antibodies of this invention can also be used for affinity chromatography in isolating the receptor. Columns can be prepared where the antibodies are linked to a solid support, e.g., particles, such as agarose, Sephadex, or the like, where a cell lysate may be passed through the column, the column washed, followed by increasing concentrations of a mild denaturant, whereby the purified receptor protein will be released.

The GRP receptor of this invention is particularly useful in kits and assay methods which are capable of screening compounds for binding activity to the GRP receptor. Several methods of automating assays have been developed in recent years so as to permit screening of tens of thousands of compounds per year. The development of suitable assays can be greatly facilitated by the availability of large amounts of purified, soluble receptor in an active state such as is attainable by the process of this invention.

A kit for determining the binding affinity of a test compound to the gastrin releasing peptide receptor would typically comprise a test compound; a labeled compound, for example a ligand or antibody having known binding affinity for the gastrin releasing peptide receptor; a source of gastrin releasing peptide receptor; and a means for separating bound from free labeled compound, such as a solid phase for immobilizing the gastrin releasing peptide receptor.

Once compounds are screened, those having suitable binding affinity to the GRP receptor can be evaluated in suitable biological assays, as are well known in the art, to determine whether they act as agonists or antagonists.

This invention is particularly useful for screening compounds by using the recombinant GRP receptor in any of a variety of drug screening techniques. The advantages of using the recombinant GRP receptor in screening for GRP receptor reactive drugs include: (a) improved renewable source of the receptor from a specific source; (b) potentially greater number of receptors per cell giving higher signal to noise ratio in assays; and (c) receptor subtype specificity (theoretically giving greater biological and disease specificity).

One method of drug screening utilizes eukaryotic or prokaryotic host cells which are stably transformed with recombinant DNA molecules expressing the GRP receptor. Such cells, either in viable or fixed form, can be used for standard receptor/ligand binding assays. Competitive assays are particularly useful, where the cells (source of GRP receptor) are contacted and incubated with a labeled ligand having known binding affinity to the GRP receptor, such as $^{125}$I-GRP, and a test compound whose binding affinity to the GRP receptor is being measured. The bound ligand and free ligand are then separated to assess the degree of ligand binding. The amount of test compound bound is inversely proportional to the amount of ligand binding measured. Any one of numerous techniques can be used to separate bound from free ligand to assess the degree of ligand binding. This separation step could typically involve a procedure such as adhesion to filters followed by washing, adhesion to plastic followed by washing, or centrifugation of the membranes. Viable cells could also be used to screen for the effects of drugs on GRP receptor mediated functions, for example, second messenger levels (Ca), proliferation, etc.

Another method utilizes membranes from transformed eukaryotic or prokaryotic host cells as the source of the GRP receptor. These cells are stably transformed with DNA vectors directing the expression of the GRP receptor. Essentially, the membranes would be prepared from the cells and used in any receptor/ligand binding assay such as the competitive assay set forth above.

Still another approach is to use solubilized, unpurified or solubilized, purified receptors from transformed eukaryotic or prokaryotic host cells. This allows for a real "molecular" binding assay with the advantages of increased specificity, the ability to automate, and high test drug throughput.

Another technique for drug screening involves an approach which provides high throughput screening for compounds having suitable binding affinity to the gastrin releasing peptide receptor and is described in detail in Geysen, European Patent Application 84/03564 published on Sep. 13, 1984. First, large numbers of different small peptide test compounds are synthesized on a solid substrate such as plastic pins or some other surface. Then all the pins are reacted with solubilized, unpurified or solubilized, purified GRP receptor and washed. The next step involves detecting bound GRP receptor.

Purified GRP receptor can be coated directly onto plates for use in the aforementioned drug screening techniques. However, non-neutralizing antibodies to the GRP receptor can be used as capture antibodies to immobilize the GRP receptor on the solid phase.

This invention also contemplates the use of competitive drug screening assays where neutralizing antibodies to the receptor or receptor fragments compete with a test compound for binding to the receptor. In this manner the antibodies can be used to detect the presence of any polypeptide which shares one or more binding sites of the GRP receptor and can also be used to occupy binding sites on the receptor that might otherwise be occupied by gastrin releasing peptide.

Additionally, neutralizing antibodies against the receptor and soluble fragments of the receptor which contain the high affinity ligand binding site, can be used to inhibit gastrin releasing peptide receptor function in cancerous tissues.

This invention also contemplates use of the GRP receptor, fragments thereof, peptides, and their fusion products in a variety of diagnostic kits and methods for detecting the presence of the gastrin releasing peptide receptor.

A kit for determining the concentration of gastrin releasing peptide receptor in a sample would typically comprise a labeled compound (ligand or antibody) having known binding affinity for the gastrin releasing peptide receptor, a source of gastrin releasing peptide receptor and a means for separating the bound from free labeled compound, for example a solid phase for immobilizing the gastrin releasing peptide receptor.

A method for determining the concentration of gastrin releasing peptide receptor in a sample would typically comprise the steps of: (1) preparing membranes from a sample comprised of a GRP receptor source; (2) washing the membranes and suspending them in a buffer; (3) solubilizing the GRP receptor by incubating the membranes in a culture medium to which a detergent and a soluble cholesteryl ester has been added; (4) adjusting the detergent concentration of the solubilized receptor; (5) contacting and incubating said dilution with radiolabeled GRP to form GRP:GRP receptor complexes; (6) recovering the complexes such as by filtration through polyethyleneimine treated filters; and (7) measuring the radioactivity of the recovered complexes.

Antibodies specific for the receptor or receptor fragments are useful in diagnostics to detect the presence of elevated levels of the receptor and/or its fragments. Such diagnostic assays can employ lysates, fixed cells, immunofluorescence, and further can involve the detection of antigens related to the GRP receptor in serum, or the like. Diagnostic assays may be homogeneous (without a separation step between free reagent and receptor-ligand complex) or heterogeneous (with a separation step). Various commercial assays exist, such as radioimmunoassay (RIA), enzyme-linked immunosorbent assay (ELISA), enzyme immunoassay (EIA), enzyme-multiplied immunoassay technique (EMIT), substrate-labeled fluorescent immunoassay (SLFIA) and the like. For example, unlabeled antibodies can be employed by using a second antibody which is labeled and which recognizes the antibody to the GRP receptor or to a particular fragment thereof. These assays have also been extensively discussed in the literature.

Frequently, the reagents for diagnostic assays are supplied in kits, so as to optimize the sensitivity of the assay. For the subject invention, depending upon the nature of the assay, the protocol, and the label, either labeled or unlabeled antibody, or labeled receptor is provided, usually in conjunction with other additives, such as buffers, stabilizers, materials necessary for signal production such as substrates for enzymes, and the like. Desirably, the reagents are provided as a dry powder, where the reagents may be reconstituted in an aqueous medium having appropriate concentrations for performing the assay.

Any of the aforementioned constituents of the drug screening and the diagnostic assays may be used without modification or may be modified in a variety of ways. For example, by labeling such as covalently or non-covalently joining a moiety which directly or indirectly provides a detectable signal. In any of these assays, the ligand, test compound, GRP receptor, or antibodies thereto can be labeled either directly or indirectly. Possibilities for direct labeling include label groups which include: radiolabels such as $^{125}$I, enzymes (U.S. Pat. No. 3,645,090) such as peroxidase and alkaline phosphatase, and fluorescent labels (U.S. Pat. No. 3,940,475) capable of monitoring the change in fluorescence intensity, wavelength shift, or fluorescence polarization. Possibilities for indirect labeling include biotinylation of one constituent followed by binding to avidin coupled to one of the above label groups.

There are also numerous methods of separating the bound from the free ligand, or alternatively the bound from the free test compound. The receptor can be immobilized on various matrixes followed by washing. Suitable matrixes include plastic such as an ELISA plate, filters, and beads. Methods of immobilizing the receptor to a matrix include direct adhesion to plastic, use of a capture antibody, chemical coupling, and biotin-avidin. The last step in this approach involves the precipitation of receptor/ligand complex by any of several methods including those utilizing an organic solvent such as polyethylene glycol or a salt such as ammonium sulfate. Other suitable separation techniques include, without limitation, the fluorescein antibody magnetizable particle method described in S. J. Rattle et al., Clin. Chem. 30(9):1457–1461 (1984) and the double antibody magnetic particle separation as described in U.S. Pat. No. 4,659,678.

The methods for linking protein receptors or their fragments to the various labels have been extensively reported in the literature and do not require detailed discussion here. Many of the techniques involve the use of activated carboxyl groups either through the use of carbodiimide or active esters to form peptide bonds, the formation of thioethers by reaction of a mercapto group with an activated halogen such as chloroacetyl, or an activated olefin such as maleimide, for linkage, or the like.

Another diagnostic aspect of this invention involves use of oligonucleotide and polynucleotide sequences taken from the GRP receptor sequence which can be used as probes for detecting levels of the gastrin releasing peptide receptor in patients suspected of having cancer. The preparation of both RNA and DNA nucleotide sequences, the labeling of the sequences and the preferred size of the sequences has received ample description and discussion in the literature. Normally an oligonucleotide probe should have at least about 14 nucleotides, usually at least about 18 nucleotides, and the polynucleotide probes may be up to several kilobases. Various labels may be employed, most commonly radionuclides, particularly $^{32}$P. However, other techniques may also be employed, such as using biotin modified nucleotides for introduction into a polynucleotide. The biotin then serves as the site for binding to avidin or antibodies, which may be labeled with a wide variety of labels, such as radionuclides, fluorescers, enzymes, or the like. Alternatively, antibodies may be employed which can recognize specific duplexes, including DNA duplexes, RNA duplexes, DNA-RNA hybrid duplexes, or DNA-protein duplexes. The antibodies in turn may be labeled and the assay carried out where the duplex is bound to a surface, so that upon the formation of duplex on the surface, the presence of antibody bound to the duplex can be detected. The use of probes to the novel anti-sense RNA may be carried out in any conventional techniques such as nucleic acid hybridization, plus and minus screening, recombinational probing, hybrid released translation (HRT) and hybrid arrested translation (HART). This also includes amplification techniques such as polymerase chain reaction (PCR).

This invention has significant therapeutic value. It is expected that the GRP receptor, fragments thereof and antibodies thereto, along with compounds identified as having binding affinity to the GRP receptor, will be useful in the treatment of cancerous tissues such as prostatic and pancreatic tumors, and in the treatment of small cell lung cancer. Additionally, it is further believed that this invention will have therapeutic value in any disease or disorder associated with abnormal expression or abnormal triggering of the GRP receptor. For example, it is believed that the GRP receptor plays a role in neurologic function, and can affect gastrointestinal, pulmonary, and brain tissue.

Drug screening using the GRP receptor or fragments thereof can be done to identify compounds having binding affinity to the GRP receptor. Subsequent biological assays can then be utilized to determine if the compound has intrinsic stimulating activity and is therefore a blocker or antagonist in that it blocks the activity of gastrin releasing peptide. Likewise, a compound having intrinsic stimulating activity can activate the receptor and is thus an agonist in that it simulates the activity of gastrin releasing peptide. This invention further contemplates the therapeutic use of antibodies to the GRP receptor as antagonists.

The GRP receptor (recombinant), fragments thereof, and antibodies to the receptor or its fragments, antagonists, and agonists, may be administered directly to the host to be treated or depending on the size of the compounds, it may be desirable to conjugate them to carrier proteins such as ovalbumin or serum albumin prior to their administration. Therapeutic formulations may be administered in any conventional dosage formulation. While it is possible for the active ingredient to be administered alone, it is preferable to present it as a pharmaceutical formulation. Formulations comprise at least one active ingredient as defined above together with one or more acceptable carriers thereof. Each carrier must be both pharmaceutically and physiologically acceptable in the sense of being compatible with the other ingredients and not injurious to the patient. Formulations include those suitable for oral, rectal, nasal, or parenteral (including subcutaneous, intramuscular, intravenous and intradermal) administration. The formulations may conveniently be presented in unit dosage form and may be prepared by any methods well known in the art of pharmacy. The therapy of this invention may be combined with or used in association with other chemotherapeutic or chemopreventive agents.

The broad scope of this invention is best understood with reference to the following examples, which are not intended to limit the inventions in any manner.

EXAMPLE 1

Preparation of House 3T3 Fibroblast Membranes

Mouse Swiss 3T3 fibroblasts were grown to confluence in Dublecco's modified Eagles medium supplemented with 10% (vol/vol) fetal calf serum in T-850 roller bottles (lots of 100) at 37° C. in a 10% $CO_2$/90% air environment. Upon harvest, the medium was poured off and each bottle was rinsed twice with 50 ml calcium/magnesium free phosphate buffered saline (PBS-CMF). Cells were incubated with 25–30 ml 0.04% (wt/vol) EDTA in PBS-CMF (warmed to 37° C.) for 15 minutes at room temperature. The cells were then removed with firm knocks and pipetted into conical 250 ml centrifuge tubes on ice. Cells from six roller bottles were combined into each centrifuge tube. Roller bottles were rinsed a final time with 25 ml PBS-CMF. Cells were pelleted at 1800 rpm for 10 minutes at 4° C. in a Sorvall RC-3B centrifuge. Each pellet was resuspended in 50 ml fresh PBS-CHF at 4° C. Cells from 2–3 centrifuge tubes were combined, pelleted and washed with an additional 120 ml PBS-CMF. The final cell pellets were resuspended in 200 ml lysis buffer (50 mM HEPES. pH 7.5, 2 Mm $MgCl_2$. 1 mM EGTA, 50 µg/ml leupeptin, 2.5 µg/ml pepstatin. 10 µg/ml aprotinin and 0.5 mM phenylmethylsulfonyl fluoride (PMSF)). Cells were lysed by $N_2$ cavitation. Briefly, 100 ml of the cell suspension was placed in ice in a sealed stainless steel container which was pressurized to 900 psi of $N_2$. The suspension was slowly released from the chamber through a small orifice into a collection tube, causing rapid decompression and lysis of the cells. Cell lysis appeared complete by microscopic visualization. Membranes were pelleted at 39,000×g for 30 minutes at 4° C., resuspended in lysis buffer and pelleted again. The pellet was suspended at a concentration of 15 mg membrane protein/ml in a storage buffer (50 mM HEPES, pH 7.5, 1 mM EGTA, 0.25M sucrose, 50 µg/ml leupeptin, 2.5 µg/ml pepstatin, 10 µg/ml aprotinin and 0.5 mM PMSF). Membranes were aliquoted in volumes of 1 and 5 ml, flash-frozen in liquid $N_2$, and stored at −80° C.

EXAMPLE 2

Comparison of Detergents for Solubilization of the GRP Receptor

Figure 1:
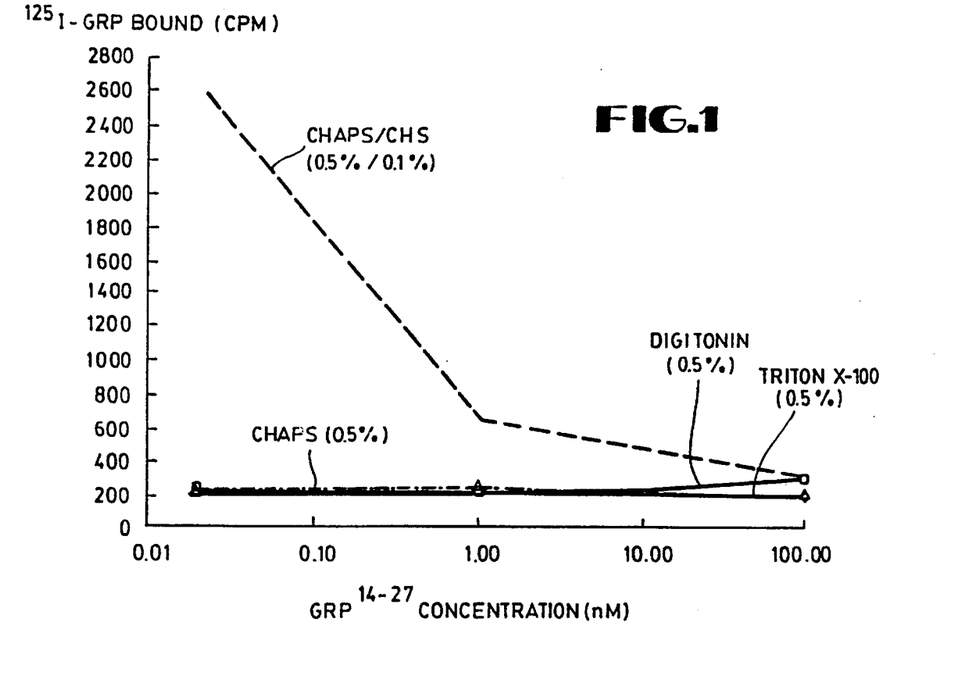
FIG. 1 is a graphical comparison of the ability of several detergents to solubilize the GRP receptor and shows the effect of solubilization on binding activity.

Several detergents employed for receptor extraction in other systems were tested to measure their ability to solubilize GRP receptor from Swiss 3T3 fibroblast membranes. Digitonin, Triton X-100, CHAPS, and CHAPS with CHS were all used to extract membranes at a detergent concentration of 0.50% and all were effective in solubilizing receptor that had been radio-labeled by cross-linking to $^{125}$I-GRP. The binding of $^{125}$I-GRP (0.02 mM), measured as counts/minute (CPM) bound, was assayed in the presence of the detergent (0.1%) used in the extraction and several concentrations of the unlabeled 14-27 C-terminal amino acids of GRP (GRP14-27), as is shown in FIG. 1. Only extraction with CHAPS plus CHS yielded detectable binding activity. Since all detergents were effective in solubilizing the GRP receptor, the failure to observe binding activity in extracts prepared with digitonin, Triton X-100 and CHAPS, was a result of receptor inactivation during the solubilization process. It was noted however, that partial reactivation of the receptor extracted with CHAPS (without CHS) could be achieved by subsequent addition of CHS. This established that CHS acts as a stabilizer in promoting the active GRP receptor.

Comparison of Detergent Concentration for Solubilization of the GRP Receptor

Figure 2:
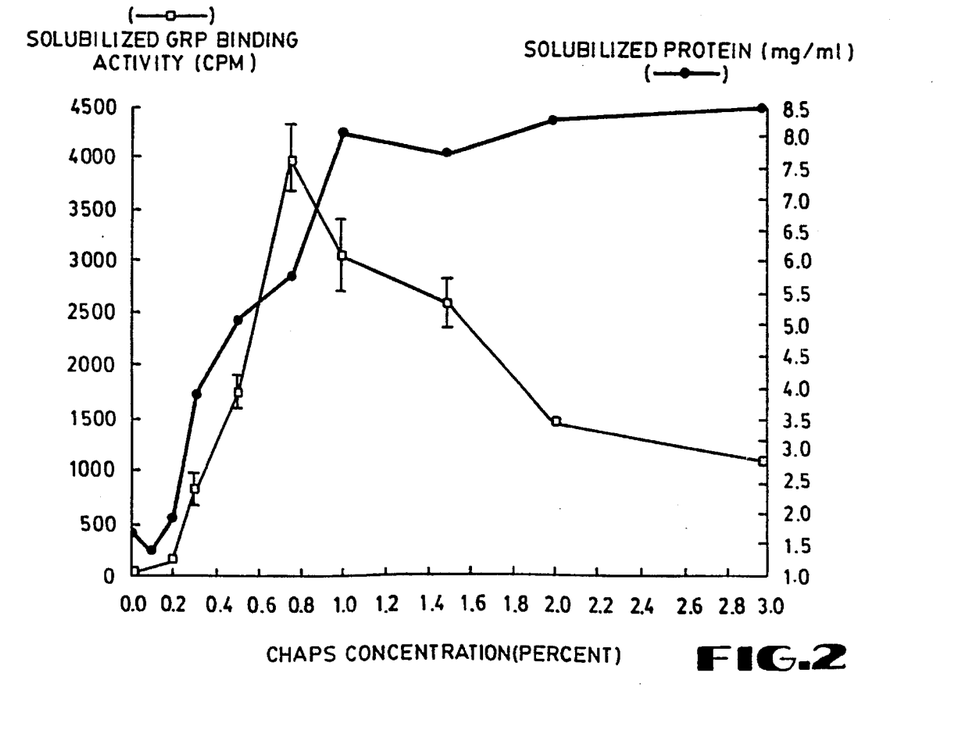
FIG. 2 is a graph of GRP binding activity and GRP receptor solubilization as a function of detergent (CHAPS) concentration.

Swiss 3T3 fibroblast membranes, prepared as in Example 1, were incubated with various concentrations of the detergent CHAPS. After separation of insoluble material by centrifugation, soluble GRP binding activity was measured in the supernatant. When 0.75% (w/v) CHAPS was used to solubilize the GRP receptor, maximal receptor binding was observed, as is shown in FIG. 2. However, to obtain maximal solubilization of protein, CHAPS concentration of 1.0% (w/v) or greater were required. The GRP receptor binding declined steadily at higher detergent concentrations. In order to observe specific GRP binding to receptors solubilized by CHAPS, it was necessary to include the stabilizing agent CHS. The ratio of CHAPS:CHS was maintained at 10:1 under both extraction and assay conditions.

Figure 3:
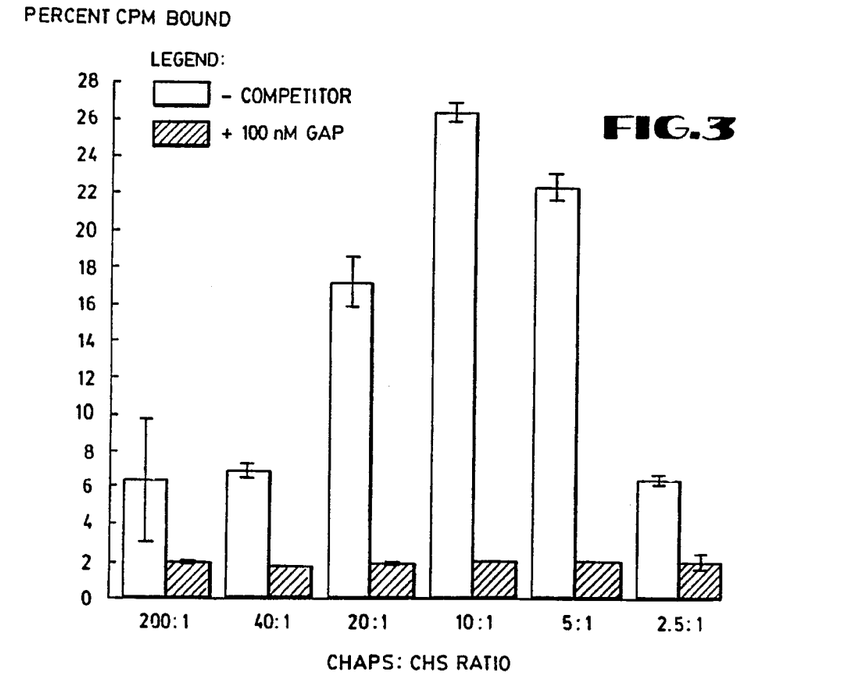
FIG. 3 is a graph of GRP receptor solubilization and activity as a function of the soluble cholesteryl ester stabilizing agent (CHS) concentration.

Comparison of Stabilizing Agent Concentration for Solubilization of the GRP Receptor Swiss 3T3 fibroblast membranes, prepared as in Example 1, were solubilized with 0.75% (w/v) CHAPS in the presence of various amounts of cholesteryl hemisuccinate (CHS). After the removal of insoluble material by centrifugation, soluble GRP receptor binding activity was measured in the supernatant at a 0.075% (w/v) CHAPS concentration and a CHS concentration 10 fold less than that used in the solubilization step. As shown in FIG. 3, the optimal ratio of CHAPS to CHS was about 10:1.

Figure 4:
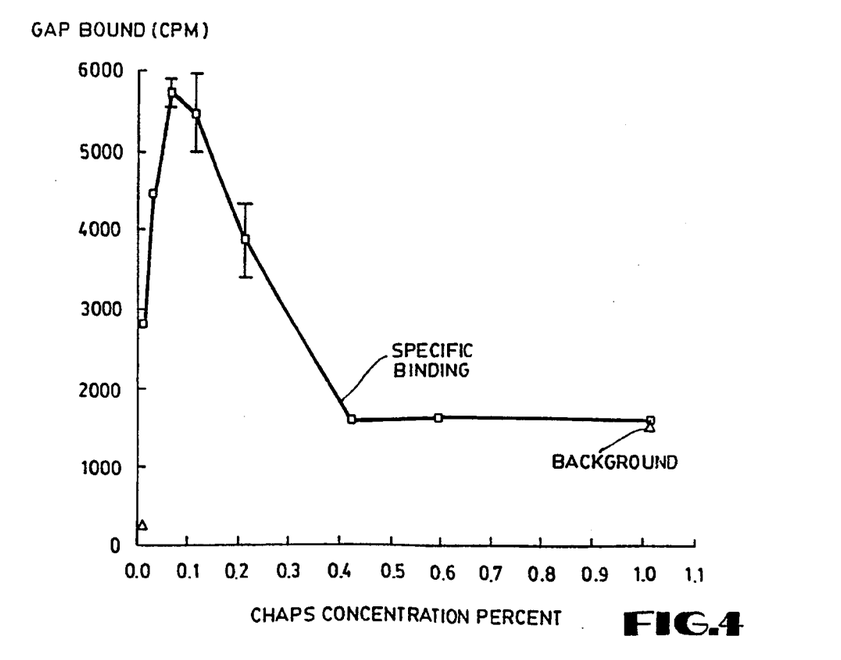
FIG. 4 is a graph of GRP binding activity as a function of detergent (CHAPS) concentration.

Comparison of Detergent Concentration for Binding Activity of the Solubilized GRP Receptor The dependency of binding activity on the concentration of detergent was studied. As is shown in FIG. 4, GRP binding to the receptor has a narrow optimum between 0.075% and 0.1% CHAPS, and specific binding falls dramatically at CHAPS concentrations greater than 0.4%. Detergent levels above a concentration of 0.4% also cause a large increase in the nonspecific background in the assay which is possibly due to the formation of detergent aggregates. While the GRP receptor is maximally extracted from membranes with detergent levels that are highly inhibitory (0.75%), the inactivation of receptor molecules by CHAPS appeared to be reversible. Complete binding activity of the receptor incubated in 0.75% CHAPS and 0.15% CHS could be recovered upon reducing the concentration of detergent by dialysis.

Optimum pH for GRP Binding $^{125}$I-GRP binding was determined in 500 μl of 20 mM MES, 20 mM CHES, 20 mM HEPES, 2 mM EDTA, 10 mg/ml BSA, 30 μg/ml bacitracin, 0.02 nM $^{125}$I-GRP and 5 μg CHAPS extracted membrane protein at several pH values, ranging from pH 5–10. After incubation at 15° C. for 30 minutes, samples were cooled on ice. This was followed by the addition of 5.0 mL of 50 mM HEPES, pH 7.5, to normalize the pH before the separation of bound and free ligand. Receptor binding was found to be optimal at a pH of 7.5. However, the receptor was able to tolerate incubation at a pH of 10 for at least 24 hours at 4° C. without loss of activity. In contrast, incubation of the receptor with a pH 5 buffer at 4° C. caused a rapid loss of binding activity.

EXAMPLE 3

Solubilization of the GRP Receptor for Assays

Swiss 3T3 fibroblast membranes, prepared in Example 1, were suspended at 15 mg protein/ml in 50 mM HEPES, pH 7.5, 1.0 mM EGTA, 100 mM NaCl, 0.25M sucrose, 50μg/ml leupeptin, 5 μg/ml pepstatin, 10 μg/ml aprotinin, 30 μg/ml bacitracin, and 0.5 mM phenylmethylsulfonyl fluoride. A mixture of 3-[(3-cholamidopropyl) dimethylammonio]-1-propane sulfonate (CHAPS) and cholesteryl hemisuccinate (CHS) in a ratio of 10:1 was added slowly to yield a final concentration of 0.75% CHAPS. The extract was incubated at 21° C. for 30 minutes, cooled to 4° C. and the insoluble material was removed by centrifugation at 100,000×gravity for 60 minutes. The clear supernatant was frozen in liquid $N_2$ and stored at −80° C. without loss of activity.

EXAMPLE 4

Ligand Binding Assays

Specific $^{125}$I-GRP (3-($^{125}$Iodotyrosyl$^{15}$) gastrin releasing peptide, 1900–2000 Ci/mmol) binding to intact or detergent solubilized membranes (20–50 μg, prepared as in Example 3) was assayed in 50 mM HEPES, pH 7.5, 2 mM EDTA, 10 mg/ml bovine serum albumin (BSA), 30 μg/ml bacitracin, and 0.02 nM $^{125}$I-GRP. For assays of detergent solubilized membrane extracts, the final CHAPS detergent concentration was adjusted to between 0.050% and 0.20%. The concentration of CHS was maintained at ⅕ to 1/10 the concentration of CHAPS. Samples were also prepared omitting the BSA. After incubation at 15° C. for 30 minutes, samples were cooled to 0° C. Bound ligand ($^{125}$I-GRP:GRP receptor complex) was recovered by rapid filtration through polyethyleneimine treated Whatman GF/B filters, followed by four washes with 4 mls of ice cold Tris buffer (50 mM Tris/Cl, pH 7.5). The filters were counted in an Isodata 500 gamma counter. Nonspecific backgrounds were determined by inclusion of 100 nM unlabeled GRP in the assay to compete for specific binding sites and typically represented 1.5–2% of the specific radioactivity bound. The nonspecific binding could be attributed to a small degree of binding of the $^{125}$I-GRP to the filters. It was found that binding activity of the solubilized receptor is highly dependent on the concentration of the detergent. As shown in FIG. 4, GRP binding to the receptor has a narrow optimum between 0.075% CHAPS/0.015% CHS and 0.10% CHAPS/0.02% CHS, and specific binding falls dramatically at CHAPS/CHS concentrations greater than 0.4%/0.08%. Detergent levels above about 0.4% CHAPS with 0.08% CHS present also cause a large increase in the nonspecific background possibly due to the formation of detergent aggregates. Since the receptor is maximally extracted from membranes with detergent levels that are highly inhibitory (0.75% CHAPS), inactivation of the receptor by CHAPS appeared to be reversible. Indeed, complete binding activity of receptor incubated in 0.75% CHAPS plus 0.15% CHS could be recovered upon reducing the concentration of detergent by dialysis.

EXAMPLE 5

Receptor Kinetics

Assays were performed for various times of incubation and BSA (10 mg/ml) was either included in the assay or omitted. $^{125}$I-GRP binding to the soluble receptor at 15° C. leveled off by 20 minutes and remained constant for up to 2 hours. Omission of the BSA that had been added to prevent proteolysis of the ligand had no significant effect on the binding kinetics.

EXAMPLE 6

G Protein Complex

The GRP receptor in Swiss 3T3 fibroblast membranes was found to be G protein coupled. Therefore, the effect of guanylnucleotides on $^{125}$I-GRP binding to soluble receptors was studied. The final detergent concentration was 0.075% CHAPS and 0.015% CHS was present. The G protein coupling of the GRP receptor in intact Swiss 3T3 fibroblast membranes was inferred from the observation that the ligand affinity of the receptor was reduced about ten fold in the presence of the nucleotides GDP and GTP and the non-hydrolyzable GTP analogue GMPPNP. In the presence of $Mg^{+2}$, guanylnucleotides are presumed to induce the dissociation of G proteins from the high affinity ligand/receptor/G protein ternary complex, resulting in formation of the ligand/receptor complex that displays lower affinity. The GRP receptor extracted from membranes by CHAPS showed no change in their ligand binding properties in the presence of $Mg^{+2}$ and GTP or GMPPNP at levels that reduce GRP binding to membranes by about 80%. The lack of an effect of GTP on GRP binding in the presence of $Mg^{+2}$ indicates that interaction of the receptor with its G protein is not maintained in the detergent extract. The control in the following table, contains $MgCl_2$.

| Guanylnucleotide | Counts/minute Bound Measured as % of Total Added |
|---|---|
| Solubilized Membranes | |
| control | 28 |
| control + 10 μM AMPPNP | 27.8 |
| control + 10 μM GTP | 27.5 |
| control + 10 μM GMPPNP | 26.5 |
| control + 10 μM GMPPNP + 100 nM GRP1-27 | 2.0 |
| Intact Membranes | |
| control | 28.7 |
| control + 5 μM ATP | 29.7 |
| control + 5 μM MPPNP | 33.4 |
| control + 5 μM GTP | 10.7 |
| control + 5 μM GMPPNP | 10.5 |
| control + 5 μM GMPPNP + 100 nM GRP1-27 | 1.4 |

EXAMPLE 7

Scatchard Analysis of the Soluble GRP Receptors

Scatchard analysis of $^{125}$I-GRP binding to intact and solubilized Swiss 3T3 membranes was done. One particular experiment is discussed below, where the binding parameters of the solubilized and the membrane bound form of the receptor are determined under similar conditions. Assays were determined at 15° C. For assays of solubilized or intact membranes, the binding reactions were terminated at 30 and 180 minutes, respectively. The following are the binding parameters, where $K_D$ is the dissociation constant and $B_m$ is the maximum binding capacity:

$K_D$ (intact membranes)=37 pM $K_D$ (solubilized membranes)=10 pM $B_m$ (intact membranes)=0.79 pmol/mg protein $B_m$ (solubilized membranes)=1.0 pmol/mg protein Scatchard analysis revealed the presence of a high affinity binding site. Some non-linearity and scatter in the data was observed at low values of bound/free ligand where determination of precise binding data is most difficult. The dissociation constant of the ligand binding to the soluble receptors (10 pM) was less than that exhibited by the receptors in intact membranes (37 pM) despite the lack of G protein coupling to the soluble receptors that was observed. As noted above, such G protein coupling boosts the affinity of the membrane receptors by an order of magnitude. However, the assay was performed under conditions that had been optimized for GRP binding to the soluble receptor which may have compensated for the affinity lost by G protein interactions. In other experiments, the dissociation constant of the solubilized receptor was calculated to range from 10 pM to 30 pM. The data demonstrated that the functional conformation of the receptor binding site was maintained in detergent solution.

The Scatchard data from this experiment also indicated that there were 0.79 pmol receptors/mg protein in crude Swiss 3T3 cell membranes and about 50% of the receptor binding sites were solubilized by extracting the membranes with detergent. Some of the factors that were found to be necessary for the most efficient solubilization of receptor activity were inclusion of NaCl (>100 mM), elimination of divalent cations and the extraction of membranes at room temperature. Although NaCl was necessary for the optimal solubilization of the receptors, the salt inhibited GRP binding to both the Swiss 3T3 fibroblast membranes and detergent solubilized receptor ($IC_{50}$=approx. 50 mM). However, the inhibition of the receptors by NaCl at concentrations up to 1.0M was found to be completely reversible.

EXAMPLE 8

Ligand Specificity of GRP Binding Sites in Soluble Membrane Extracts

The binding of $^{125}$I-GRP to solubilized 3T3 membranes was assayed in the presence of various unlabeled competitor peptides. The C-terminal eight amino acids of GRP (GRP20-27) were found to be essential for high affinity binding to the GRP receptors in whole cells. The complete GRP sequence (GRP1-27), the N-terminal portion of GRP (GRP1-16), substance P, substance P antagonist, physalemin (all of which were from Peninsula Laboratories, Belmont Calif.), and the C-terminal portion of GRP with norleucine substituted for methionine referred to as [Nle$^{14,27}$]GRP13-27 ((i.e. Lys-Nle-Tyr-Pro-Arg-Gly-Asn-His-Trp-Ala-Val-Gly-His-Leu-Nle-NH$_2$), were tested for their ability to compete for $^{125}$I-GRP binding to soluble 3T3 fibroblast membrane extracts. The concentration of [Nle$^{14,27}$]GRP13-27 required to cause 50% inhibition of $^{125}$I-GRP binding to the soluble receptor ($IC_{50}$=0.3 nM) was slightly higher than that of GRP1-27 ($IC_{50}$=0.1 nM). In contrast, the N-terminal portion (GRP1-16) was unable to compete with $^{125}$I-GRP for binding to the soluble receptor. Additionally, substance P, substance P antagonist and physalemin had no inhibitory effect at the concentrations tested (up to 1000 nM). These results parallel closely that which was found in similar studies in whole cells and isolated membranes.

EXAMPLE 9

Cross-linking of $^{125}$I-GRP Receptors

Figure 5:
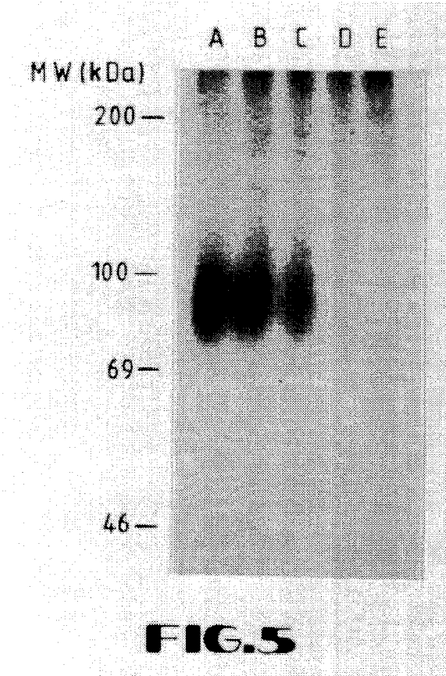
FIG. 5 is a gel display of SDS-PAGE analysis of $^{125}$I-GRP cross-linked to the GRP receptor in a crude soluble extract.

The molecular weight of the GRP receptor in solubilized Swiss 3T3 membranes was estimated by covalently cross-linking it to bound $^{125}$I-GRP via the homobifunctional cross-linking reagent bis(sulfosuccinimidyl) suberate (BS$^3$) and analyzing the affinity of labeled receptor by SDS-PAGE (sodium dodecyl sulfate-polyacrylamide gel electrophoresis). This cross-linker is specific for primary amino groups. Soluble 3T3 fibroblast membrane protein (40 μg) was incubated for 30 minutes at 15° C. in a final volume of 500 μl of 50 mM HEPES, 2 mM EDTA, 0.075% CHAPS, 0.015% CHS, 30 μg/ml bacitracin, and 0.2 nM $^{125}$I-GRP. The binding reaction was cooled to 0° C. and BS$^3$ was added to yield a final concentration of 3 mM. Cross-linking was quenched by addition of 0.10 ml of Tris buffer (1.0M Tris/Cl, pH 7.5). After another 10minute incubation, 0.1 ml TCA (100%) was added and the solution was further incubated at 0° C. for 30 minutes. Precipitated material was collected by centrifugation, washed with ice cold acetone, and heated at 95° C. for 3 minutes in SDS-PAGE sample buffer. The samples were subjected to SDS-PAGE on a 7.5% gel and the gel was fluorographed. A detailed description of the SDS-PAGE technique is found in Laemmli et al., Nature 227:680 (1970), which is incorporated herein by reference. FIG. 5 illustrates the gel display.

| Lane | Composition |
| --- | --- |
| A | no addition |
| B | 0.1 nM unlabeled GRP |
| C | 0.5 nM unlabeled GRP |
| D | 1.0 nM unlabeled GRP |
| E | 100 nM unlabeled GRP |

A strongly labeled species migrated in a diffuse band with an apparent $M_r$ of about 75–100 kDa. Low levels of unlabeled GRP inhibited the labeling of this species, indicating that the labeling is highly specific. The broadness of the labeled band is consistent with the fact that the GRP receptor has been found to contain carbohydrate. The labeled product is very similar to that derived from whole cell or membrane cross-linking experiment. N-Glycanase treatment of samples derived from cross-linked whole cells indicated that the labeled protein contained N-linked carbohydrates. The deglycosylated protein displayed an apparent $M_r$ of 38 kDa on SDS-PAGE.

EXAMPLE 10

Purification of the GRP Receptor Solubilization of the GRP Receptor

Swiss 3T3 fibroblast membranes (2–3 g of protein) were prepared as described in Example 1 and suspended in 200 ml storage buffer (see Example 1). The membranes were mixed with 50 ml of NaCl (5.0M), bringing the NaCl concentration to about 1M, pelleted by centrifugation at 40,000×g for 30 minutes, and washed twice at 4° C. with 200 ml of high salt buffer (50 mM HEPES, pH 7.5, 2 mM EDTA, 1.0M NaCl, 25 µg/ml aprotinin 10 µg/ml aprotinin, 2.5 µg/ml pepstatin and 0.5 mM PMSF). The membranes were then washed with low salt buffer (50 mM HEPES, pH 7.5, 2 mM EDTA, 25 µg/ml leupeptin, 10 µg/ml aprotinin, 2.5 µg/ml pepstatin and 0.5 mM PMSF) and resuspended in 200 ml 50 mM HEPES, pH 7.5, 2 mM EDTA, 1 mM EGTA, 100 mM NaCl, 0.03 mg/ml bacitracin, 25 µg/ml leupeptin, 10 µg/ml aprotinin, 2.5 µg/ml pepstatin and 0.5 mM PMSF. A stock solution containing a mixture of CHAPS and CHS was added slowly to the membranes to give a final concentration of 0.75% CHAPS and 0.075% CHS. The mixture was incubated for 30 minutes at 21° C., cooled to 4° C. and centrifuged at 100.000×g for 60 minutes at 4° C. The supernatant contained the solubilized GRP receptor.

Precipitation by Polyethylene Glycol

To the solubilized extract (190 ml), 126 ml of ice cold polyethylene glycol (PEG) 8,000 (50 w/v % in $H_2O$) was added. After thorough mixing, the precipitate that formed was collected by centrifugation at 100.000×g for 10 minutes. The pellet was suspended in 25 mM HEPES, 25 mM Tris, pH 7.5, 2 mM EDTA, 0.075% CHAPS, 0.0075% CHS, 5 µg/ml leupeptin and 10 µg/ml bacitracin in a total volume of 50 ml with the aid of a Potter-Elvehjem homogenizer. The suspension, which contained some insoluble protein, was centrifuged at 69,000×g for 10 minutes, and the pellet was discarded.

Wheat Germ Agglutinin Chromatography

Following precipitation by PEG, the GRP receptor was further purified by lectin affinity chromatography. A column (1.6×9 cm) containing wheat germ agglutinin-agarose resin (3–5 mg lectin/mg of wet gel) (E-Y Laboratories, San Mateo, Calif.) was equilibrated with 50 mM HEPES, pH 7.5, 2 mM EDTA, 0.25% CHAPS, 0.025% CHS, 5 µg leupeptin and 10 µg bacitracin at 4° C. The soluble extract was diluted with one volume of column buffer, and the final detergent concentration was adjusted to 0.25% CHAPS and 0.025% CHS. The sample was applied to the lectin column at a flow rate of 1.5 ml/min. The column was then washed with about 10 column volumes of buffer, and eluted with column buffer plus 5 mM N,N',N"-triacetyl-chitotriose. Fractions containing the GRP receptor binding activity were pooled and diluted with 2.3 volumes of 25 mM HEPES, 25 mM Tris, pH 7.5, 2.0 mM EDTA, 5 µg/ml leupeptin and 10 µg/ml bacitracin.

GRP Affinity Chromatography

Actigel superflow resin (10 ml)(Sterogene, San Gabriel, Calif.) was washed with 5 volumes of 100 mM $KPO_4$, pH 7.0. The resin was incubated with 10 ml of 100 mM $KPO_4$, 100 mM $NaCNBrH_3$, pH 7.0 containing 2 mg/ml [Nle$^{14,27}$] GRP13-27 for 2 hours with gentle agitation. The resin was washed with 100 mM $KPO_4$, pH 7.0, followed by alternating washes with 100 mM KAc, pH 4.0, 0.5M NaCl and 100 mM Tris pH 8.0, 0.5M NaCl. A column of the resin (1.6×5 cm) was equilibrated with 25 mM Tris, 25 mM HEPES, pH 7.5, 2.0 mM EDTA, 0.075% CHAPS, 0.0075% CHS, 5 µg/ml leupeptin and 10 µg/ml bacitracin at 4° C. The crude GRP receptor eluted from the lectin column was loaded onto the GRP affinity column at 0.1 ml/min. The column was then washed with about 20 volumes of the equilibration buffer. The bound receptor was eluted from the column with equilibration buffer plus 0.5M NaCl at a flow rate of 0.2 ml/min. Fractions containing the receptor were identified by assays of $^{125}$I-GRP binding activity and were pooled (10–13 ml). The elution pool was concentrated to about 1 ml by ultrafiltration using a Centriprep-10 device (Amicon, Danvers, Mass.). The sample was then desalted by dilution of the sample with 15 volumes of affinity column equilibration buffer and re-concentration of the sample to 1 ml. This desalting step was repeated and the resulting 1 ml sample was diluted to 5 ml with affinity column equilibration buffer. PAGE analysis of the purified GRP receptor revealed the presence of a significant level of contamination.

This solution of semi-pure receptor was loaded onto a second [Nle$^{14,27}$]GRP13-27-actigel superflow column (1.0×3 cm), prepared as described above, at 1.8 ml/h. The column was washed with 20 column volumes of equilibration buffer, and the bound receptor was eluted with equilibration buffer plus 0.5M NaCl at a flow rate of 0.1 ml/min. Fractions containing GRP receptor binding activity were pooled and concentrated to 0.3 ml by ultrafiltration.

Gel Filtration

The purified receptor was desalted by chromatography on a Superose-6 HR 10/30 column (Pharmacia LKB, Piscataway, N.J.). The column was equilibrated with 20 mM HEPES, pH 7.5, 2 mM EDTA, 0.075% CHAPS, 0.0075% CHS and 100 mM NaCl. The receptor was chromatographed at 0.4 ml/min. The receptor was eluted from the column in about 2 ml.

Characterization of the Purified GRP Receptor

The overall yield of the pure GRP receptor from the crude solubilized extract ranged from 10–20%, based on recovery of high affinity $^{125}$I-GRP binding activity. Scatchard analysis of binding data obtained with the purified receptor indicated that its affinity for GRP ($K_d$=10–30 pM) was essentially the same as the receptor in the crude detergent solubilized extract. The data shows that 30–50 pmoles of receptor sites are typically obtained in the final purified fractions of the receptor, as outlined in this example. This corresponds to about 1–2 µg of receptor protein, taking into account that the deglycosylated receptor exhibits an apparent molecular weight of 36±5 kilodaltons on SDS PAGE gels.

Figure 6:
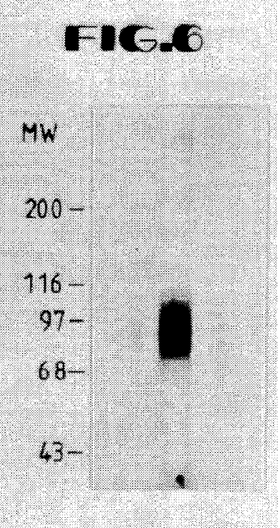
FIG. 6 is a silver stained gel display of SDS-PAGE analysis of the purified GRP receptor.

A silver stained SDS-PAGE gel of the receptor preparation showed a single intensely staining diffuse band with an apparent molecular weight of 70–100 kD. The receptor preparation was essentially free of contaminants. FIG. 6 illustrates the silver stained gel display of the purified GRP receptor. The relative level of silver staining of the GRP receptor band was compared with known amounts of protein to determine the approximate amount of receptor protein loaded on the gel. The rough value obtained was in the range of that estimated to be present by Scatchard analysis of $^{125}$I-GRP binding data, which confirmed that the intensely staining band on the gel was the GRP receptor. Furthermore, the apparent molecular weight of the purified GRP receptor corresponded to that obtained with affinity labeled receptor. This was obtained by binding $^{125}$I-GRP to the receptor in whole cells, intact membranes, or crude soluble extracts, and cross-linking the receptor-ligand complex with a homobifunctional cross-linking reagent.

The diffuse nature of the GRP receptor band on SDS PAGE is characteristic of proteins containing carbohydrate. A small portion of the purified receptor was radiolabeled by iodination with $^{125}$I-NaI in the presence of Iodogen (Pierce, Rockford, Ill.) to enhance the detection of the receptor on gels. Treatment of the radiolabeled receptor with N-glycanase resulted in loss of the 70–100 kD band, and the generation of a new band at about 36±5 kilodaltons, representing the deglycosylated receptor.

Determination of Partial Amino Acid Sequence of the GRP Receptor

A partial sequence near the N-terminus of the purified GRP receptor was determined by sequential Edman degradation. The sequence obtained for residues 8–17 was:

-Leu-Asn-Leu-Asp-Val-Asp-Pro-Phe-Leu-Ser-

We claim:

1. A purified naturally occurring gastrin releasing peptide receptor in active form, which has been solubilized from the cell membrane, and wherein said gastrin releasing peptide receptor has the following characteristics:
   (1) binds gastrin releasing peptide with an affinity of at least $K_D$=10 nM;
   (2) binds selectively with peptides of the bombesin type;
   (3) contains N-linked carbohydrates; and
   (4) when deglycosylated has an apparent molecular weight of 36 kilodaltons plus or minus 5 kilodaltons on SDS-PAGE under reducing conditions.

2. The receptor of claim 1 which is solubilized by:
   (1) preparing membranes from a gastrin releasing peptide receptor source;
   (2) washing said membranes and suspending said membranes in a buffer;
   (3) solubilizing the gastrin releasing peptide receptor by incubating a culture of said membranes in a culture medium to which a detergent and a soluble cholesteryl ester have been added; and
   (4) adjusting the detergent concentration of said gastrin releasing peptide receptor.

3. The receptor of claim 2 wherein said gastrin releasing peptide receptor source is a mammalian cell line.

4. The receptor of claim 3 wherein said cell line is mouse Swiss 3T3 fibroblasts.

5. The receptor of claim 2 wherein said detergent is 3-[(3-cholamidopropyl)dimethylammonio]-1-propane sulfonate.

6. The receptor of claim 2 wherein said soluble cholesteryl ester is cholesteryl hemisuccinate.

7. The receptor of claim 1 wherein said receptor is solubilized and purified by:
   (1) preparing membranes from a gastrin releasing peptide receptor source;
   (2) washing said membranes and suspending said membranes in a buffer;
   (3) solubilizing the gastrin releasing peptide receptor by incubating a culture of said membranes in a culture medium to which a detergent and a soluble cholesteryl ester has been added, forming a soluble extract;
   (4) precipitating the gastrin releasing peptide receptor from the soluble extract of step (3), collecting the precipitate by centrifugation and resuspending said precipitate in a buffer containing said detergent and soluble cholesteryl ester, forming a soluble extract;
   (5) applying the soluble extract of step (4) to a wheat germ agglutinin affinity column, forming an eluate;
   (6) further fractionating the wheat germ agglutinin column eluate from step (5) on a gastrin releasing peptide affinity column, forming an eluate; and
   (7) dialyzing the gastrin releasing peptide affinity column eluate from step (6) and applying said eluate to a second gastrin releasing peptide affinity column to obtain solubilized and purified gastrin releasing peptide receptor.

8. The receptor of claim 7 wherein said receptor is further purified by gel filtration following step (7).

9. The receptor of claim 7 wherein said gastrin releasing peptide source is a mammalian cell line.

10. The receptor of claim 9 wherein said cell line is Swiss 3T3 fibroblasts.

11. The receptor of claim 7 wherein said soluble cholesteryl ester
is cholesteryl hemisuccinate.

12. The gastrin releasing peptide receptor of claim 1 having the following further characteristics:
   (1) runs as a broad band under reducing conditions on SDS-PAGE with an apparent molecular weight of about 70 to 100 kilodaltons;
   (2) is free of coupled G proteins; and
   (3) has a partial amino acid sequence near the N-terminus of:

-Leu-Asn-Leu-Asp-Val-Asp-Pro-Phe-Leu-Ser-.

13. The receptor of claim 1 wherein said receptor is mammalian.

14. The receptor of claim 13 wherein said receptor is murine.

* * * * *